US010299959B2

(12) United States Patent
Behan (10) Patent No.: US 10,299,959 B2
(45) Date of Patent: May 28, 2019

(54) EYEDROPPER WITH IMPROVED STABILITY AND METHOD OF ADMINISTERING A LIQUID ONTO THE SURFACE OF AN EYE

(71) Applicant: Bullseye Dropper, LLC, Covington, KY (US)

(72) Inventor: Robert Behan, Crescent Springs, KY (US)

(73) Assignee: Bullseye Dropper, LLC, Covington, KY (US)

( * ) Notice: Subject to any disclaimer, the term of this patent is extended or adjusted under 35 U.S.C. 154(b) by 515 days.

(21) Appl. No.: 14/781,764

(22) PCT Filed: Apr. 3, 2014

(86) PCT No.: PCT/US2014/032807
§ 371 (c)(1),
(2) Date: Oct. 1, 2015

(87) PCT Pub. No.: WO2014/165664
PCT Pub. Date: Oct. 9, 2014

(65) Prior Publication Data
US 2016/0038339 A1 Feb. 11, 2016

Related U.S. Application Data

(60) Provisional application No. 61/847,074, filed on Jul. 16, 2013, provisional application No. 61/853,359, filed on Apr. 3, 2013.

(51) Int. Cl.
*A61F 9/00* (2006.01)
(52) U.S. Cl.
CPC .......... *A61F 9/0026* (2013.01); *A61F 9/0008* (2013.01)

(58) Field of Classification Search
CPC ............................ A61F 9/0008; A61F 9/0026
See application file for complete search history.

(56) References Cited

U.S. PATENT DOCUMENTS 3,058,466 A 10/1962 Routsong
3,934,590 A 1/1976 Campagna et al.
(Continued)

FOREIGN PATENT DOCUMENTS

CN 2892066 Y 4/2007
CN 201642536 U 11/2010
(Continued)

OTHER PUBLICATIONS

International Preliminary Report on Patentability issued by the International Searching Authority in corresponding International Patent Application No. PCT/US2014/032807 dated Oct. 6, 2015 (9 pages).
(Continued)

*Primary Examiner* — Kia Weng
(74) *Attorney, Agent, or Firm* — Wood Herron & Evans LLP (57) ABSTRACT

An eyedropper (2, 102) having improved stability is provided for administering a volume of liquid onto the surface of an eye (57). The eyedropper (2, 102) includes a body (4, 104) having a reservoir body (18, 118), a first foot (14, 114), a second foot (16, 116), and a nozzle (26, 126). The nozzle (26, 126) is in fluid communication with the internal cavity (24, 124) of the reservoir body (18, 118) and projecting from an outer surface (20, 120) of the reservoir body (18, 118) between the first and second feet (14, 16, 114, 116). The first and second feet (14, 16, 114, 116) are separated by a distance that is at least equal to the height of the eyedropper (2, 102).
(Continued)

In preferred embodiments, the distance between the first and second feet (14, 16, 114, 116) is greater than the height of the reservoir body (18, 118).

17 Claims, 4 Drawing Sheets

(56) References Cited

U.S. PATENT DOCUMENTS

| | | | |
|---|---|---|---|
| 4,002,168 A | | 1/1977 | Petterson |
| 4,392,590 A | * | 7/1983 | Hofmann-Igl ........ A61F 9/0026 222/174 |
| 4,733,802 A | | 3/1988 | Sheldon |
| 5,810,794 A | | 9/1998 | Peplinski |
| 6,632,202 B1 | * | 10/2003 | Hagele .................. A61F 9/0008 222/420 |
| 2010/0286633 A1 | * | 11/2010 | Marx .................... A61F 9/0026 604/296 |

FOREIGN PATENT DOCUMENTS

| | | |
|---|---|---|
| CN | 103417326 A | 12/2013 |
| WO | 2008041177 A2 | 4/2008 |

OTHER PUBLICATIONS

The State Intellectual Property Office of the People's Republic of China, Office Action issued in counterpart CN Application No. 2014800301859 dated Oct. 10, 2016, 14 pp., including English translation.

Supplemental Search Report issued by the European Patent Office in corresponding European Application No. 14780048.6 dated Mar. 7, 2016 (8 pages).

* cited by examiner

EYEDROPPER WITH IMPROVED STABILITY AND METHOD OF ADMINISTERING A LIQUID ONTO THE SURFACE OF AN EYE

CROSS-REFERENCE TO RELATED APPLICATIONS

This application is a submission under 35 U.S.C. § 371 of International Application No. PCT/US14/32807 filed Apr. 3, 2014, which claims the benefit of U.S. Application Ser. No. 61/853,359 filed on Apr. 3, 2013, and U.S. Application Ser. No. 61/847,074 filed on Jul. 16, 2013, the disclosures of which are expressly incorporated by reference herein in their entirety.

FIELD

Aspects of the invention are generally related to devices and methods for administering liquid drops onto the surface of a subject's eye. More particularly, aspects of the invention are related to an eyedropper having a structure providing improved stability to a subject when administering drops onto the surface of a subject's eye and to methods of using such an eyedropper.

BACKGROUND

Presently, eye drops come in a variety of dropper bottle shapes and sizes to administer a variety of drops into the eyes of a subject. Those devices typically have a bottle base with a nozzle attached thereto for administering the drops. Although the details may vary, the majority of eye drop bottles effectively have similar shapes, styles, and uses. Products such as Visine®, Clear Eyes® and the like, lead the field with eye drop bottles that have been used for years but are, however, antiquated.

Administration of drops into the eye is not easy with current eyedropper bottles. Most eye drop bottles currently in use are available in sizes that are able to be held in between the thumb and forefinger. The bottle is squeezed so that one or more drops are expelled from the bottle when aimed in the general direction of the eye after the head is tilted back resulting in a drop that hopefully makes its way onto the surface of the eye. If the subject administering the drop has shaky hands, such as in many elderly patients, or the subject having drops administered into his or her eyes cannot hold his head still, such as with a small child, this process can be even more difficult. Thus, presently available eyedropper bottles often result in inaccurate placement of the drop resulting in drops landing on other parts of the body surrounding the eye, on clothes, or elsewhere, which could affect the areas the drops contact. In addition, presently available eyedropper bottles can also result in multiple drops coming out instead of just one, which can cause waste. Another problem associated with presently available eyedropper bottles is the head tilt required by the user to administer the drop tends to be extreme and uncomfortable and can cause one to lose balance. Moreover, the ability to squeeze the bottle while looking up at it to keep it on target is strenuous and then attempting to look away at the right moment so that the eye drop does not hit the pupil is difficult at best. Many users need two hands to administer eye drops to themselves because they operate the eyedropper bottle with one hand while using their other hand to hold open their eyelids to assist them in administering drops onto the surface of the eye.

Previous efforts to improve eyedropper bottles have included attaching various structures to conventional bottles to improve their function. These added structures present additional shortcomings. Some devices utilize complicated mechanical structures to deliver the drop from the bottle onto the surface of the eye. Other devices require assembly onto the eyedropper bottle before use, which means that the user must keep up with the additional components. Also, these structures result in an eyedropper assembly in which the eyedropper bottle is held at a relatively large distance from the eye during use, which can significantly decrease the stability of the eyedropper assembly to the user, especially if the end user has shaky hands or has difficulty holding his or her head still.

Today's eyedropper bottles used with over the counter and prescription medications cause anxiety and or frustration to the end user. A solution to the restrictions, frustrations, discomfort, and waste of today's eyedropper bottles is needed and is hereby addressed with this invention.

SUMMARY

Aspects of the invention are directed to an eyedropper that makes it easy, safe, and effective to administer drops to the eye. The embodiments of the invention (1) are stabilized by contacting the face on opposite sides of the eye socket, such as above and below or medial and lateral the eye socket, so when the reservoir body of the eyedropper is squeezed between fingers it accurately administers a drop onto the surface of the eye, (2) can administer drops exactly where intended, (3) can administer one drop at a time, (4) can be operated with a single hand, (5) can decrease neck tilt, (6) can assist in pulling the skin below or above the eye, away from the eye socket to assist with maintaining the eyelids in an open position with one hand, (7) can reduce anxiety and or frustration in the end user, and (8) can create a satisfied user. More particularly, when in use to administer drops of varying makeup or solution, embodiments of the invention stabilize the eyedropper and some embodiments can administer a single drop at a time (or specified amount), decrease head tilt, and allow for one handed operation while decreasing anxiety of the user.

Accordingly, an eyedropper having improved stability is provided for administering a volume of liquid onto the surface of the eye. The eyedropper includes a body having a reservoir body, a first foot, a second foot, and a nozzle. The nozzle is in fluid communication with an internal cavity of the reservoir body and projects from an outer surface of the reservoir body between the first and second feet. The first and second feet are separated by a distance that is at least equal to the height of the eyedropper. In preferred embodiments, the distance between the first and second feet is greater than the height of the reservoir body.

BRIEF DESCRIPTION OF THE DRAWINGS

The accompanying drawings, which are incorporated in and constitute a part of this specification, illustrate various embodiments of the invention and, together with a general description of the invention given above and the detailed description of the embodiments given below, serve to explain the embodiments of the invention.

DETAILED DESCRIPTION

With reference to FIGS. 1 to 4, embodiments of the invention are directed to an eyedropper 2, 102 having a body 4, 104 with a first leg 6, 106 and a second leg 8, 108. The first leg 6, 106 includes a first foot 14, 114 located at one end of the body 4, 104 and the second leg includes a second foot 16, 116 at the opposite end of the body 4, 104. The body 4, 104 also includes a reservoir body 18, 118 intermediate to the first and second feet 14, 114, 16, 116. The reservoir body 18, 118 includes an outer surface 20, 120 and an inner surface 22, 122 defining a portion of an internal cavity 24, 124. The eyedropper 2, 102 also includes a nozzle 26, 126 projecting from the outer surface 20, 120 of the reservoir body 18, 118 between the first and second feet 14, 16, 114, 116. The nozzle 26, 126 is in fluid communication with the internal cavity 24, 124.

Figure 1:
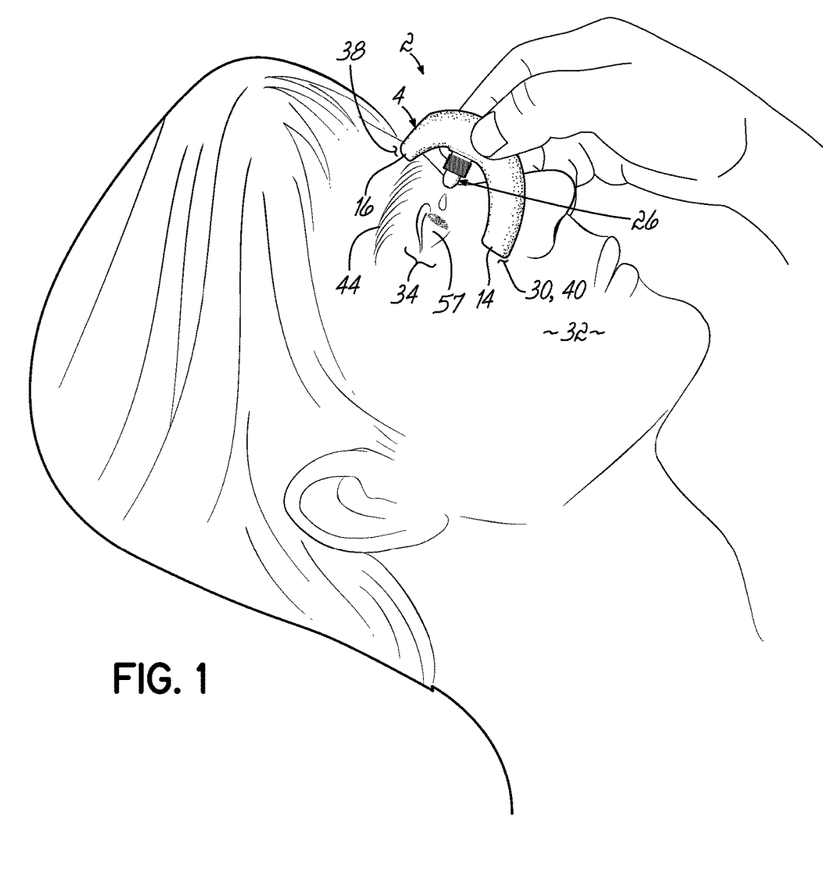
FIG. 1 illustrates the use of an embodiment of an eyedropper in accordance with embodiments of the invention.

The first foot 14, 114 has a first end surface 28 configured to contact a first area 30 of a subject's face 32 adjacent the subject's eye socket 34 (FIG. 1). The second foot 16, 116 has a second end surface 36 configured to contact a second area 38 of the subject's face 32 on the opposite side of the eye socket 34. In an embodiment, the first foot 14, 114 is configured to contact the subject's face 32 below the eye socket 34, such as on or near the cheek 40, and the second foot 16, 116 is configured to contact the subject's face 32 at a location above the eye socket 34, such as on or near the eye brow 44 (FIG. 1). The first foot 14, 114 may alternatively contact a first area 30 on the subject's face generally lateral to the eye socket 34, such as on or near the temple area, and the second foot 16, 116 may contact a second area medial to the eye socket 34, such as on or near the bridge of the nose.

Figure 2:
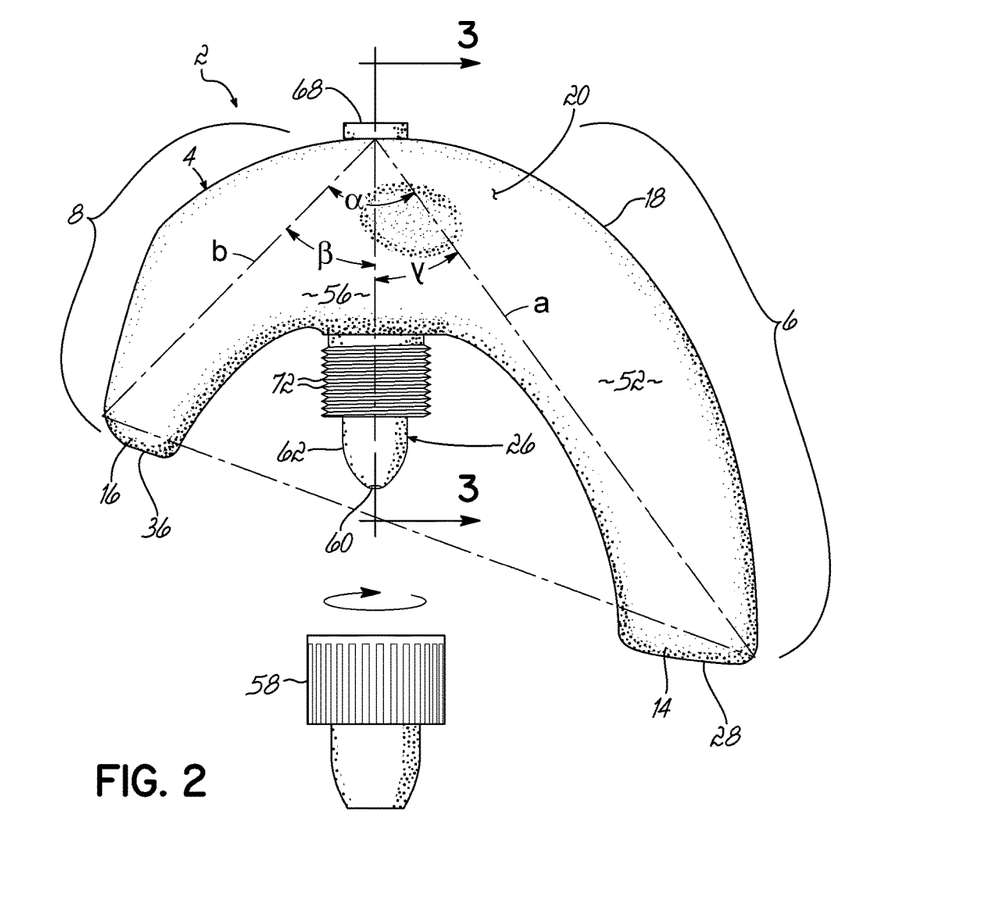
FIG. 2 is a partially disassembled side view of an exemplary embodiment of an eyedropper in accordance with embodiments of the invention.

The relationship between the first foot 14, 114, and the second foot 16, 116, which may be defined at least in part by the angle between the first leg 6, 106, and the second leg 8, 108 may be defined relative to a first axis a associated with the first leg 6, 106, a second axis b associated with the second leg, and a third axis c associated with the nozzle 26, 126. The third axis c is defined by the longitudinal axis of the nozzle 26, 126 and projects along a center line through the tip 62, 162 of the nozzle 26, 126 to a point that intersects the outer surface 20, 120 of the body 4, 104 that overlies the nozzle 26, 126. The first axis a is defined by a line extending through the length of the first leg 6, 106 from the point along the outer surface 20, 120 of the first leg 6, 106 or first foot 14, 114 that is the greatest distance in a straight line from the intersection of the third axis c with the outer surface 20, 120 of the body 4, 104. The second axis b is defined by a line extending through the length of the second leg 8, 108 from the point along the outer surface 20, 120 of the second leg 8, 108 or second foot 16, 116 that is the greatest distance in a straight line from the intersection of the third axis c with the outer surface 20, 120 of the body 4, 104. Thus, the first, second, and third axes intersect at a point on the outer surface 20, 120 opposite the nozzle 26, 126 and may be used to define the angular relationship between the first and second legs 6, 8, 106, 108 and the nozzle 26, 126. The intersection of the first axis a with the second axis b forms an angle α that is less than 180 degrees, and preferably is in a range from about 45 degrees to about 175 degrees, and more preferably from about 90 degrees to about 160 degrees (FIG. 2). The intersection of the first leg 6, 106 with the second leg 8, 108 may be defined by the intersection a first axis a with the second axis b and the third axis c. The angle α formed by the intersection of the first axis a with the second axis b is bisected by the third axis c. The angle β between the second axis b and the third axis c is typically less than or equal to the angle γ between the first axis a and the third axis c. Preferably, the angle β is less than the angle γ.

In an embodiment of the invention, the nozzle is closer to one of the first or second feet 14, 16, 114, 116 than it is to the other foot. For example, in the exemplary embodiments shown in FIGS. 1 to 4, the first axis a of the first leg 6 has a first length and the second axis b of the second length that is less than the first length of the first axis a. The first length of the first axis a may be about 1.1 to about 2 times the second length of the second axis b, or the first length may be about 1.2 to about 1.8 times the second length, or the first length may be about 1.3 to about 1.7 times second length. In another embodiment of the invention, the nozzle 26, 126 equidistant between the first and second feet 14, 16, 114, 116. In such an embodiment, the first length of the first axis a is approximately equal to the length of the second axis b.

Figure 4:
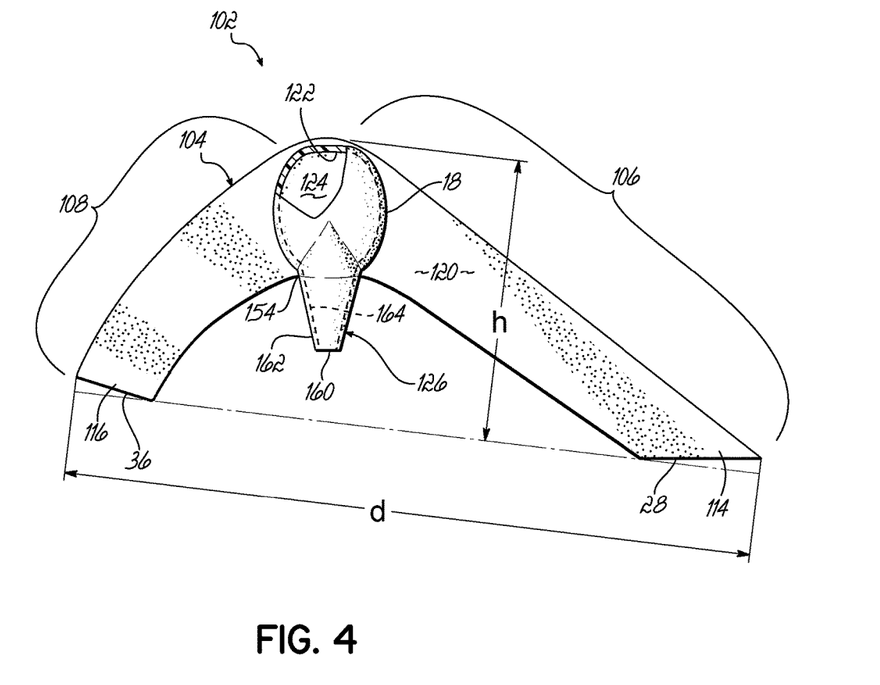
FIG. 4 is a side view of an alternative exemplary embodiment of an eyedropper in accordance with embodiments of the invention.

Another aspect of the invention is the significantly improved stability conferred by the relationship between the height of the eyedropper 2, 102 and the distance between the first 14, 114 and second 16, 116 feet. A distance d between the first foot 14, 114 and the second foot 16, 116 is measured from the outer most edge of the eyedropper as shown in FIG. 4. The height of the eyedropper is the vertical distance between a first plane that is tangential to both the first and second feet and a second plane that is tangential to a point along the outer surface of the body 4, 104 that is parallel to the first plane and that is the greatest vertical distance from the first plane. The distance d is at least equal to the height h of the eyedropper, and preferably the distance d is greater than the height h. In exemplary embodiments, the distance d between the first and second feet 114, 116 of the eyedropper 2, 102 may range from about 4.5 inches to about 2.5 inches. Preferred exemplary embodiments have a distance d of about 4.5 inches, or about 3.1 inches, or about 2.5 inches. The height h of the eyedropper 2, 102 is less than or equal to the distance d and can range from about 1.5 inches to about 2.5 inches. In preferred exemplary embodiments, the height h is about 2.5 inches or about 2 inches, or about 1.5 inches. The ratio of the distance d to height h is at least 1 and preferably greater than 1. The ratio of the distance d to height h may range between about 1 to about 3 or about 1.1 to about 3 or about 1.5 to about 3.

The reservoir body 4, 104 has a width w that is perpendicular to the length of the body along the first and second axes a, b. In exemplary embodiments, the width w can range from about ½ inch to about 1½ inches or from about ½ inch to about 1¼ inches, or from about ⅞ of an inch to about 1 inch.

The reservoir body has an internal cavity 24, 124, which is defined by its inner surface 22, 122. In the exemplary embodiment illustrated in FIGS. 2 and 3, the internal cavity 24 extends from the first foot 14 through the first leg 6 and through the second leg 8 to the second foot 16. In this embodiment, the reservoir body 18 is generally continuous with the first and second legs 6, 8 from the first foot 14 to the second foot 16. This structure provides a reservoir body with a relatively large volume for storing the liquid to be dispensed onto the surface of the eye while maintaining the desired relationship between the height of the eyedropper 2 and the distance d between the first and second feet 14, 16.

In an alternative embodiment, reservoir body does not extend through one or both of the first and second legs toward one or both of the first and second feet, i.e., the at least one of the first or second feet are separated from the reservoir body a solid portion of the leg or a portion of the leg into which the liquid to be dispensed cannot pass. In the exemplary embodiment shown in FIG. 4, the reservoir body 118 does not extend a significant distance into either of the first leg 106 or the second leg 108. Instead, the reservoir body 118 is coupled to the first foot 114 by a solid first leg 106 and is coupled to the second foot 116 by a solid second leg 108. While the first and second legs 106, 108 are described in this exemplary embodiment as solid, they could also be hollow or have openings along their length. In a further alternative embodiment, the reservoir body may extend partially into one or both of the first and second legs.

Figure 3:
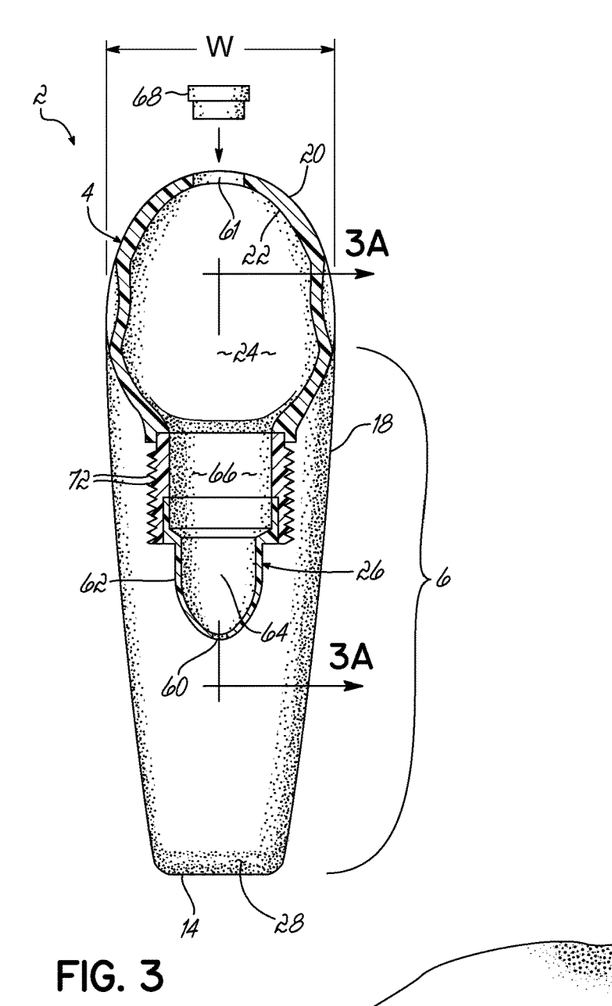
FIG. 3 is a cross-sectional view of the exemplary embodiment of the eyedropper in FIG. 2 taken along line 3-3.
Figure 3A:
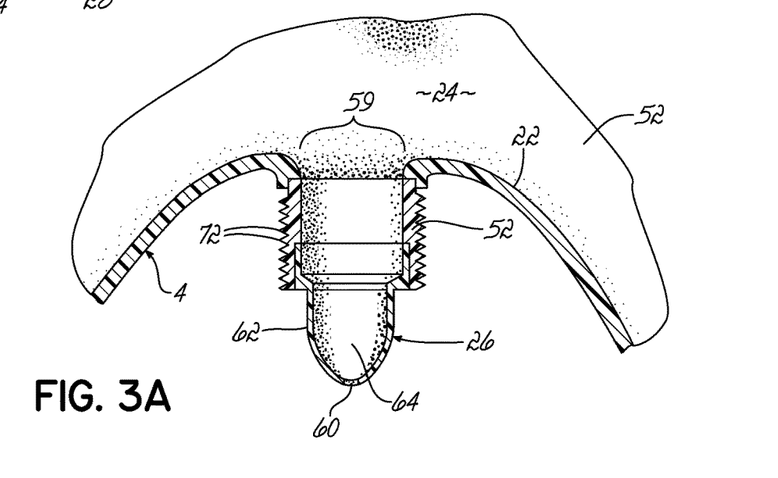
FIG. 3A is a cross-sectional view of the exemplary embodiment of the eyedropper in FIG. 3 taken generally along line 3A-3A.

In the exemplary embodiment shown in FIGS. 2 and 3, the internal cavity 24 of the reservoir body 18 includes a reservoir portion 52 nearer the first foot 14 in the first leg 6 and a liquid administering portion 56 located nearer the second foot 16 and adjacent the nozzle 26. The reservoir portion 52 is configured to store a volume of liquid whereas the liquid administering portion 56 is configured to allow for a volume of liquid to be dispensed from the nozzle 26 onto the surface of the eye 57. The liquid stored in the reservoir body 18 may fill both the reservoir portion 52 and the liquid administering portion 56 or may fill just the reservoir portion 52.

The inner surface 22 of the reservoir body 18 presents a relatively smooth surface over which the liquid to be administered may flow toward the nozzle 26. Preferably, the inner surface 22 near the nozzle 26 includes a funnel-shaped portion 59 that leads toward the nozzle 26. The funnel-shaped portion 59 may present a curved surface or a frustoconical surface. The funnel-shaped portion 59 increases the ease with which the user of the eyedropper 2 can utilize the entire contents of the eyedropper because the funnel-shaped portion 59 directs droplets of liquid to the nozzle 26.

The nozzle 26, 126 projects from the outer surface 20, 120 of the reservoir body 18, 118 and is located between the first and second feet 14, 16, 114, 116. The nozzle 26, 126 includes a channel 64, 164 passing between an opening 60, 160 in the tip 62, 162 of the nozzle 26, 126 to the base 54, 154 of the nozzle 26, 126 that allows for a liquid to be administered to the surface of the eye from the internal cavity 24, 124. The base 54, 154 of the nozzle 26, 126 is coupled to the reservoir body 18, 118 so as to project downwardly from the eyedropper 2, 102 toward the eye when the first and second feet 14, 16 are in contact with the face 32 of the subject (FIG. 1). The tip 62, 162 of the nozzle 26, 126 is situated relative to the first and second feet 14, 16, 114, 116 such that the tip 62, 162 is less likely to contact the eye 57. To accomplish this, the tip 62, 162 of the nozzle 26, 126 does not extend through a plane that is tangential to both the first and second feet 14, 16, 114, 116. The external surface of the nozzle 26 may optionally include a structure for engaging and retaining a cap 58 over the nozzle 26, such as threads 72 for engaging threads on an internal surface of the nozzle cap 58.

The reservoir body 18, 118 is ultimately filled with a liquid prior to use. The reservoir body 18 may optionally include an opening 61 into internal cavity 24 that may be used for filling the internal cavity with a liquid to be administered onto the surface of the eye. The opening 61 may be located along the outer surface 20, such as in the outer curved surface opposite the nozzle 26 as shown in FIGS. 2 and 3, or may be located on or near the first and second feet 14, 16, or along a side of the reservoir body 4. The opening 61 may be closed such as with a cap 68 or may be blocked with a septum that may be punctured such as with a needle for filling with a syringe. In the alternative, the reservoir body 18, 118 may be filled through the nozzle 26, 126 or through the opening into which the nozzle is placed during manufacturing.

In embodiments of the invention, the base 54 of the nozzle 26 optionally includes a nozzle reservoir 66 having a predetermined volume for administering a predetermined volume liquid through the channel 64 and opening 60 of the nozzle 26. In an embodiment, the volume of the nozzle reservoir 66 may be, for example, in a range of about 5 microliters to about 25 microliters, or in a range of about 5 microliters to about 15 microliters, or preferably about 15 microliters. During use, the nozzle reservoir 66 is filled by tilting the eyedropper 2 such that liquid fills the nozzle reservoir 66 and then tilting the eyedropper so that the excess liquid falls into the reservoir portion 52 of the internal cavity 24 of the eyedropper 10. When the nozzle reservoir 66 is full, the eyedropper is considered into be loaded. The loaded eyedropper 2 is then positioned over the eye with the first and second feet 14, 16 contacting the subject's face on opposite sides of the eye socket (FIG. 1). Once positioned, the subject applies pressure to the outer surface 20 of the reservoir body 4 causing a temporary increase in the pressure of the internal cavity 24, thereby expelling the predetermined volume of liquid in the nozzle reservoir 66 from the nozzle 26. Thus, embodiments of the eyedropper 2 may accurately administer predetermined volumes of liquid onto the surface of the eye. A similar process is used to administer drops from embodiments that do not utilize a nozzle reservoir for administering a predetermined volume of liquid. For example, the exemplary embodiment shown in FIGS. 2 and 3 may be filled with a volume of liquid such that the reservoir portion 52 and the liquid administering portion 56 are both filled with liquid. In that situation, there is no need for loading the optional nozzle reservoir. Similarly, in the exemplary embodiment shown in FIG. 4, which is typically intended for single use, the reservoir body 118 is located directly above the nozzle 126, so there is no need for the optional nozzle reservoir.

Accurately delivering a predetermined volume of liquid to the surface of the eye is advantageous because the capacity of the eye 57 to hold a volume liquid is limited and drops having a volume that is greater than the eye's capacity will overflow the eye. Current eyedropper systems administer drops having a volume that exceed the volumetric capacity of the eye. The excess liquid administered to the eye either passes through the tear duct or is swept onto the face when the subject blinks his or her eye. The nozzle reservoir 66 allows for drops to be administered at a predetermined volume that does overflow the volumetric capacity of the eye, such as in a range of about 5 microliters to about 25 microliters, or in a range of about 5 microliters to about 15 microliters, or preferably about 15 microliters. An additional advantage of delivering a predetermined volume is that medicines that must be administered at a specific dose into the eye, such as antibiotic drops and medications to treat glaucoma, can be more precisely administered with less waste, which could save a subject a significant amount of money during the course of treatment.

Embodiments of the invention may include a volume of liquid to administer a plurality of drops. For example, the internal cavity of the eyedropper may range from about 5 milliliters to about 30 milliliters of liquid or range from about 7 milliliters to about 15 milliliters. In another embodiment, the internal includes a volume of liquid sufficient for a single use, such as about 25 microliters or less, or in a range from about 5 microliters to about 25 microliters. Preferably, volume is in a range of about 15 microliters or less, or in a range of about 5 microliters to about 15 microliters. In this embodiment, a plurality of eyedroppers may be packaged together, such as with breakaway structures, wherein each eyedropper includes a volume of liquid sufficient for a single administration of liquid onto the surface of the eye.

Embodiments of the invention may be made using standard blow molding techniques used with thermoplastic materials. The body of the eyedropper is made of a material having sufficient flexibility to allow the user to increase the internal pressure in the body to expel a drop of liquid from the tip while providing enough support to the body so that the eyedropper is stabilized when the first and second feet 14, 16, 114, 116 are in contact with the subject's face. A preferred plastic material is polypropylene. The tip may be made from the same material as the body or may be made from a different material. The tip may be less flexible than the body. The tip may be co-molded with the body or formed separately. In an exemplary method, the body 4 is formed by blow molding. The nozzle is formed in a separate operation. The nozzle is then inserted into an opening in the body formed to accept the nozzle. The outer surface of the portion of the body that accepts the nozzle may be threaded to receive a cap. If the tip is formed separately from the body, it may be joined to the body with known methods, such as with a friction fit, using an adhesive, or by welding. Preferably, the reservoir end of the nozzle does not project above or interfere with the operation of the funnel-shaped portion 59.

While the exemplary embodiments of the invention described herein are shown having an arched crescent-shaped structure, the function of stabilizing the eyedropper 2, 102 by contacting the face 32 on opposite sides of the eye socket 34 with the first and second feet 14, 16, 114, 116 during administration of drops may be accomplished with non-arching structures. For example, reservoir body 18, 118 could have legs 6, 8, 106, 108 of varying shapes such as straight legs, curved legs, bent legs and combinations thereof so long as the legs 6, 8, 106, 108 allow the feet to contact the subject's face 32 on opposite sides of the eye socket 34 and that the distance d between the feet 14, 16, 114, 116 is greater than or equal to height h of the eyedropper 2, 102.

While the exemplary embodiments shown herein are illustrated as having two feet, additional feet could be utilized. For example, a third or fourth leg having a third or fourth foot could be utilized. Moreover, one or both of the first and second legs could be configured to accommodate a third or fourth foot, such as by splitting the leg along a portion of its length near the feet.

In use, the first foot 14, 114 contacts a first area 30 on the subject's face below or lateral to the eye socket 34 such as on or near the cheek 40 or the temporal area, and a second area 38 on the opposite side of the eye socket 34 such as on or near the eyebrow 44 or the nose, thereby creating a stable situation to administer the drops onto the surface of the eye 57 (FIG. 1). The hand administering the drop no longer waves freely above the eye 57 (like with current eyedroppers) but is instead stabilized by the first and second feet contacting the face on opposite sides of the eye socket.

Additional stability is provided by the height h of the eyedropper 2, 102 relative to the distance d between the first and second feet 14, 16, 114, 116, which results in the eyedropper 2, 102 being relatively close to the face 32. The relative short height h compared to the distance d between the two feet 14, 16, 114, 116 allows the user to contact his or her face 32 with other parts of his or her hand, such as his other fingers or the outer edges of the palm, to act as an additional point of stability. The stability control conferred by the current structure is a major advantage not provided by eyedroppers previously available. In addition, in embodiments in which the nozzle 26, 126 is positioned closer to the second foot 16,116, than the first foot 14, 114, head tilt required when administering drops onto the surface of the eye 57 is reduced while also decreasing distance of drop fall. If desired, the structure of the eyedropper 2, 102 may assist the user in holding the eye 57 open by applying a downward pressure on the eyedropper 2, 102 after contacting the face 32 below the eye 57 with the first foot 14, 114 before contacting the face 32 above the eye 57. This all happens in a matter of seconds.

Embodiments of the invention are designed for on target performance, creating a high rate of success getting the desired liquid into the eye and can alleviate anxiety during administration of drops. Embodiments of the invention allow "on the go" application of drops. Embodiments of the invention also decrease the likelihood of contaminating the tip of the nozzle because the position of the nozzle relative to the first and second feet prevents the nozzle from contacting with the eye or surrounding tissue during use. Embodiments of the invention can also be used by children, teens, adults, and elderly with great ease.

While the present invention has been illustrated by the description of specific embodiments thereof, and while the embodiments have been described in considerable detail, it is not intended to restrict or in any way limit the scope of the appended claims to such detail. The various features discussed herein may be used alone or in any combination. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of the general inventive concept.

What is claimed is:

1. An eyedropper for administering a volume of liquid onto the surface of an eye, the eyedropper comprising:
   a body having a reservoir body with an internal cavity, a first foot, located at the base of the first leg, a second foot, located at the base of the second leg, and a nozzle in fluid communication with the internal cavity and projecting from an outer surface of the reservoir body between the first and second feet, wherein the first and second feet are separated by a distance, measured by a longitudinal length between the outer most edges of the first and second feet, that is at least equal to a height of the eyedropper, measured by the vertical distance between a first tangential plane between the first and second feet, and a second plane that is tangential to a point along the outer surface of the body
   wherein the internal cavity of the reservoir body extends into at least one of the first leg or the second leg.

2. The eyedropper of claim 1 wherein the ratio of the distance between the first and second feet and the height of the eyedropper is in a range from 1 to 3.

3. The eyedropper of claim 1 wherein the first leg has a length and the second leg has a length, and the length of the first leg is greater than the length of the second leg.

4. The eyedropper of claim 1 wherein the distance between the first and second feet is greater than the height of the eyedropper.

5. The eyedropper of claim 1 wherein the distance between the first foot and the second foot is such that the first foot is configured to contact the face of a subject adjacent one side of an eye socket and the second foot is configured to contact the face of the subject on the opposite side of the eye socket from the first foot.

6. The eyedropper of claim 1 wherein the first foot is configured to contact the face of a subject below the eye socket and the second foot is configured to contact the face above the eye socket.

7. The eyedropper of claim 1 wherein the first foot is configured to contact the face of the subject lateral to the eye socket and the second foot is configured to contact the face of the subject medial to the eye socket.

8. The eyedropper of claim 1 wherein the distance between the first and second feet is in a range from 2.5 inches to 4.5 inches.

9. The eyedropper of claim 1 wherein the height is in a range from 1.5 inches to 2.5 inches.

10. The eyedropper of claim 1 wherein the nozzle includes a reservoir portion configured to receive a predetermined volume of liquid for administering to the surface of the eye of the subject.

11. The eyedropper of claim 10 wherein the predetermined volume is in a range between 5 microliters and 25 microliters.

12. The eyedropper of claim 1 wherein the nozzle does not extend beyond a plane that is tangential to both the first and second feet.

13. The eyedropper of claim 1 wherein the first leg has a first axis and the second leg has a second axis and the intersection of the first axis with the second axis at a point on the outer surface of the body directly opposite the nozzle forms an angle facing the nozzle that is less than 180 degrees.

14. The eyedropper of claim 13 wherein the angle is between 45 degrees and 175 degrees.

15. A method for administering liquid drops onto the surface of the eye comprising:
 providing an eyedropper in accordance with claim 1;
 contacting a first portion of the face with the first foot of the eyedropper,
 contacting a second portion of the face on an opposite side of an eye socket with the second foot of the eyedropper;
 increasing the internal pressure in the internal cavity of the reservoir body of the eyedropper, wherein the pressure is increased so as to expel a volume of liquid from the nozzle on the reservoir body.

16. The method of claim 15 wherein the volume of liquid is a predetermined volume of liquid.

17. The method of claim 15 further comprising tilting the eyedropper in a first direction to fill a nozzle reservoir with the volume of liquid; and
 tilting the eyedropper in a second direction to collect liquid not in the nozzle reservoir in the body reservoir prior to expelling the volume of liquid.

* * * * *